(12) United States Patent
Cheung et al.

(10) Patent No.: US 6,395,697 B1
(45) Date of Patent: *May 28, 2002

(54) DIPHENYL BASED SOLVENTS IN BLOOMING TYPE GERMICIDAL HARD SURFACE CLEANERS

(75) Inventors: Tak Wai Cheung, Princeton Junction; Dennis Thomas Smialowicz, Waldwick, both of NJ (US)

(73) Assignee: Reckitt Benckiser Inc., Wayne, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/261,691

(22) Filed: Mar. 3, 1999

(30) Foreign Application Priority Data

Apr. 14, 1998 (GB) ................................................ 9807668

(51) Int. Cl.[7] .............................. C11D 9/42; C11D 3/48; C11D 9/50; A61L 2/00; A61L 9/00
(52) U.S. Cl. ........................ 510/382; 510/382; 510/383; 510/385; 422/28; 422/37; 424/49; 514/901
(58) Field of Search .................................. 510/382, 383, 510/385; 422/28, 37; 424/49; 514/901

(56) References Cited

U.S. PATENT DOCUMENTS

| 3,787,181 A | * | 1/1974 | Dellian et al. | .................. 8/174 |
| 4,980,153 A | * | 12/1990 | Jackson et al. | ............... 424/52 |
| 5,733,952 A | * | 3/1998 | Geoffrey | ..................... 523/143 |

FOREIGN PATENT DOCUMENTS

| EP | 0 278 660 A1 | 8/1988 | ............. A61K/7/00 |
| WO | WO97/06230 | 2/1997 | ............. C11D/1/65 |
| WO | WO97/18285 | 5/1997 | ............. C11D/1/68 |

OTHER PUBLICATIONS

Copy of PCT International Search Report for PCT Application No. PCT/US99/05958 dated Jul. 6, 1999.

* cited by examiner

Primary Examiner—Robert J. Warden, Sr.
Assistant Examiner—Imad Soubra
(74) Attorney, Agent, or Firm—Fish & Richardson, P.C.

(57) ABSTRACT

Aqueous concentrated liquid disinfectant compositions which include: an antiseptic compound other than a quaternary ammonium compound having germicidal properties; organic solvent constituent; binary co-solvent system comprising alkyl biphenyl solvent and a co-solvent; optionally but desirably at least one optional constituents. The concentrate compositions feature excellent blooming characteristics.

10 Claims, No Drawings

DIPHENYL BASED SOLVENTS IN BLOOMING TYPE GERMICIDAL HARD SURFACE CLEANERS

The present invention relates to disinfectant compositions. More particularly the present invention relates to concentrated liquid disinfectant compositions which are normally diluted in a larger volume of water to form a working solution therefrom, and which exhibit a blooming effect when diluted.

Blooming is a property exhibited by dilutable compositions such as known cleaning compositions, specifically pine-oil type cleaning compositions which contain a significant amount (generally at least about 5% and more) of pine oil. Certain phenolic disinfectant compounds, such as LYSOL disinfectant concentrate (Reckitt & Colman, Inc., Montvale N.J.) also exhibit such a blooming property. Blooming may be characterized as the formation of milky, creamy or cloudy appearance which is manifested when a dilutable composition is added to a larger volume or quantity of water. Blooming is an important characteristic from a consumer standpoint as it provides a visual indicator and impression to the consumer that the concentrated product contains active cleaning and/or disinfecting constituents which are released upon addition of the concentrate to a volume of water. Such is an important visual indicator of apparent efficacy of a concentrated product.

It has now been found that it is now possible to produce certain concentrate compositions utilizing these selected constituents in particular formulations which provide blooming type cleaning compositions in a concentrated liquid form which provide both a germicidal effect and a good blooming effect. The "blooming" observed may be described as the change of the water's appearance from essentially colorless and transparent to that of a milky white or milky yellowish white, cloudy appearance. This effect is also sometimes referred to as the "break". Such blooming is a highly desirable in blooming type cleaning compositions as consumer/end user expectations associate cleaning effectiveness with the extent and degree of this blooming upon formation of a cleaning composition. Such blooming is particularly desirable in compositions where the blooming characteristic in an aqueous dilution is long lasting.

Accordingly it is an object of the invention to provide an aqueous concentrated liquid disinfectant composition which blooms when added to a larger volume of water which comprises the following constituents:

an antiseptic agent which imparts a germicidal characteristic to the composition,
other than a quaternary ammonium compound having germicidal properties;
organic solvent constituent;
binary co-solvent system comprising alkyl biphenyl solvent and a co-solvent;
optionally but desirably at least one optional constituent selected from chelating agents, coloring agents, light stabilizers, fragrances, thickening agents, hydrotropes, pH adjusting agents, pH buffers as well as one or more detersive surfactant constituents particularly non-ionic and amphoteric surfactants, as well as others known the art and useful in similar compositions. The one or more optional constituents are selected to be present, and are included in amounts which do not undesirably affect the overall blooming characteristics of the present inventive compositions.

In preferred embodiments the concentrate compositions provide excellent initial blooming characteristics in 'as mixed' dilutions with water, but also exhibit good retention of blooming characteristics over a longer time period, viz., days and weeks.

It is a further object of the invention to provide such a concentrated liquid disinfectant composition wherein the composition exhibits a blooming effect when diluted in a larger volume of water.

It is a yet further object of the invention to provide such a concentrated liquid disinfectant composition wherein the composition exhibits a germicidal effect in both its concentrated form, and in an aqueous diluted form.

It is a still further object of the invention to provide such a concentrated liquid disinfectant composition which in a diluted form provides disinfection of surfaces wherein the presence of gram positive type pathogenic bacteria such as *Staphylococcus aureus*, and/or the presence of gram negative type pathogenic bacteria such as *Escherichia coli* and/or *Pseudomonas aeruginosa* is suspected.

It is a still further object of the invention to provide working solutions formed from concentrated liquid disinfectant compositions which exhibit a blooming effect when diluted in a larger volume of water, particularly where the dilutions retain their blooming characteristic over an extended period, i.e., several days, and even several weeks.

It is among the further object of the invention to provide such a concentrated liquid disinfectant composition wherein the composition exhibits good long term stability, i.e., shelf stability in its concentrated form.

The concentrate compositions according to the invention include as a necessary constituent at least one antiseptic constituent, other than a quaternary ammonium compound, which antiseptic constituent provides an antibacterial or sanitizing function.

The antiseptic employed in the instant composition can be any of the known antiseptic agents which are soluble to the extent of at least about 0.5 percent w/v in water at ambient temperature, particularly those conventionally included in surgical scrub solutions. Such antiseptic agents include, for example, chloramine, iodine, iodophors such as polyvinyl pyrrolidoneiodine, and chlorhexidine and salts thereof. Suitable salts of chlorhexidine which are soluble in water at ambient temperature to the extent of at least 0.5 percent w/v are, for example, the gluconate, isethionate (2-hydroxyethanesulphonate), formate, acetate, glutamate, succinamate, monodiglycollate, dimethanesulfonate, lactate, di-isobutyrate and glucoheptonate, and of these, the gluconate is particularly preferred. Antiseptics based on phenols such as orthophenyl phenol, orthobenzylparachlorophenol, and the like may also be used. Other antiseptics include parachloro meta xylenol, hexachlorophene, 2-bromo-2-nitropropane diol, salicylanilide, 3,3',4',5-tetrachlorosalicylanilide, 3',4',5-trichlorosalicylanilide, 3,5-dibromo-3'-trifluoromethyylsalicylanilide, and 3,4,4'-trichlorocarbamilide. One particularly preferred antiseptic is 2,4,4'-trichloro-2'-hydroxydiphenyl ether, which is also generally referred to as TRICLOSAN, a compound which is well known to the art. A further particularly preferred antiseptics are those based on phenols especially orthobenzylparachlorophenol.

The antiseptic above may be present in any germicidally effective concentration. Particularly, the antiseptic may be present in the concentrate compositions in amounts of from about 0.001% by weight to up to about 15% by weight, preferably about 0.01–5% by weight, most preferably in amount of between about 0.5–6% by weight.

A further constituent according to the invention is an organic solvent which is which may also improve the miscibility of further constituents according to the present invention, including any water insoluble or poorly soluble constituents. Many useful organic solvents may be used, as long as it does not undesirably disrupt the favorable characteristics of the invention, especially the blooming characteristic. Mixtures of two or more organic solvents may also be used as the organic solvent constituent.

Useful organic solvents are those which are at least partially water-miscible such as alcohols, water-miscible ethers (e.g. diethylene glycol diethylether, diethylene glycol dimethylether, propylene glycol dimethylether), water-miscible glycol ether (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethyleneglycol or propylene glycol (e.g. propylene glycol monomethyl ether acetate) all commercially available from Union Carbide, Dow Chemicals or Hoescht. Mixtures of organic solvents can also be used.

Particularly useful organic solvents include glycols such as alkylene glycols such as propylene glycol, and glycol ethers. Examples of such glycol ethers include those having the general structure R'—O—R"—OH, wherein R' is an alkoxy of 1 to 20 carbon atoms, or aryloxy of at least 6 carbon atoms, and R" is an ether condensate of propylene glycol and/or ethylene glycol having from one to ten glycol monomer units. Examples of such useful glycol ethers include propylene glycol methyl ether, dipropylene glycol methyl ether, tripropylene glycol methyl ether, propylene glycol isobutyl ether, ethylene glycol methyl ether, ethylene glycol ethyl ether, ethylene glycol butyl ether, diethylene glycol phenyl ether, propylene glycol phenol ether, and mixtures thereof. Preferred are ethylene glycol n-butyl ether, diethylene glycol n-butyl ether, and mixtures thereof. Such glycol ethers are presently commercially available from a number of sources including in the DOWANOL™ glycol ether from The Dow Chemical Company, Midland Mich. (USA).

Further particularly useful organic solvents monohydric (straight chained or branched) primary, secondary or tertiary lower aliphatic alcohols, especially $C_1$–$C_6$ aliphatic primary and secondary alcohols, of which isopropanol is particularly preferred.

The present inventors have found that inclusion of the organic solvent constituent in amounts of about 0.001% by weight to about 50% by weight have been found to be effective in solubilizing other less water soluble constituents present in the concentrate compositions of the invention. Preferably, the organic solvent constituent is present in amounts of from 0.1–40% by weight, and most preferably from about 0.1–35% by weight.

Additionally the inventor has found the according to certain preferred embodiments the organic solvent constituent, comprises, and in certain especially preferred embodiments consist essentially of, both an alkylene glycol such as propylene glycol, and a monohydric lower aliphatic alcohol such as a $C_1$–$C_6$ aliphatic primary and secondary alcohol, especially isopropyl alcohol.

The inventive compositions further also include a binary co-solvent system comprising alkyl biphenyl solvent and a co-solvent which aids in the solubilization of the biphenyl solvent in an aqueous medium.

The alkyl biphenyl solvent is one which may be generally represented by the formula

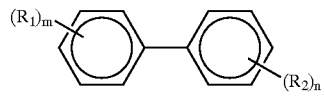

wherein:
R$_1$ is hydrogen or is a lower alkyl radical, preferably a $C_1$–$C_{10}$, but more preferably is a $C_1$–$C_6$ straight chained or branched alkyl radical,
R$_2$ is a lower alkyl radical, preferably a $C_1$–$C_{10}$, but more preferably is a $C_1$–$C_6$ straight chained or branched alkyl radical,
m is an integer from 1–3 inclusive; and,
n is an integer from 1–3 inclusive. Preferably R$_1$ is hydrogen, m is 1, and R$_2$ has any of the values indicated above.

More preferably, R$_1$ is hydrogen and m is 1, and R$_2$ is a $C_1$–$C_6$ straight chained or branched alkyl radical. It is to be understood that mixtures of the compounds indicated above may be used as the biphenyl solvent constituent.

Such alkyl biphenyls are, per se, known to the art, and are described in U.S. Pat. No. 3,787,181. Particularly useful as the alkyl biphenyl solvent are materials presently marketed as NUSOLV ABP solvents (Ridge Technologies Inc., Ridgewood N.J.) described to be a high purity alkyl biphenyls and mixtures thereof, and is also available from Koch Chemical Co. (Corpus Christi, Tex.) as SURESOL solvents.

The alkyl biphenyl solvent may be present in the concentrate compositions in amounts of from about 0.001% by weight to up to about 20% by weight, preferably about 0.01–10% by weight, most preferably in amount of between 0.1–8% by weight.

The inventors have observed that the concentrated compositions of the invention are greatly improved with the addition of a co-solvent. This co-solvent aids in the solubilization of the alkyl biphenyl solvent in water is desirably an at least partially water-miscible monohydric primary alcohol, especially a water-miscible monohydric primary $C_8$–$C_{18}$ alcohol. Particularly effective are cetyl, lauryl and myristyl alcohols. The inventors have found that the inclusion of such alcohols greatly aids in the dissolution of the alkyl biphenyl solvents in the concentrate compositions according to the invention being described herein, which aids in ensuring that clarity of the concentrate composition is maintained which is particularly desirable from a consumer standpoint.

The co-solvent may be present in the concentrate compositions in amounts of from about 0.001% by weight to up to about 5% by weight, preferably about 0.01–3% by weight, most preferably in amount of between 0.1–2% by weight.

Alternately, it is contemplated that the preferred co-solvent described above may be substituted in whole or in part by one or more nonionic or amphoteric surfactants which are also shown to aid in the dissolution of the alkyl biphenyl solvent in water. Such one or more nonionic or amphoteric surfactants include those described below.

The concentrate compositions of the invention may optionally, but in some cases very desirably include a carboxylate constituent, particularly one or more alkylpolyoxycarboxylates or alkylarylpolycarboxylates. Exemplary alkylpolyoxycarboxylates and alkylarylpolycarboxylates include alkyl- and alkylaryl-carboxylates which include those which may be represented by the general formula:

R—COO$^-$M$^+$ wherein R is a straight or branched hydrocarbon chain containing from about 9 to 21 carbon atoms, and which may also include an aromatic ring, especially a phenyl group as part of the hydrocarbon chain, and M is a metal or ammonium ion. Further preferred alkylpolyoxycarboxylates include polyethoxycarboxylates which may be represented by the general formula:

wherein R is a straight chained or branched hydrocarbon chain which may include an aryl moiety, but is desirably a straight chained or branched hydrocarbon chain; and n is an integer value of from 1–24, and M is a metal or ammonium ion, but is preferably a alkali or alkaline earth metal ion, especially sodium.

Exemplary useful alkylpolyoxycarboxylates and alkylarylpolycarboxylates include those commercially available in the NEODOX series from Shell Chemical Co.; SANDOPAN series from Clariant Inc. (Charlotte, N.C.), as well as in the SURFINE series from Finetex, Inc.

When present in the concentrated liquid disinfectant compositions, the alkylpolyoxycarboxylates or alkylarylpolycarboxylate constituent is included in amounts of from about 0.001% by weight to up to about 20% by weight, preferably about 0.1–10% by weight, most preferably in amount of between 1–5% by weight. Of course a mixture of these constituents may be used.

Water is added in order to provide 100% by weight of the concentrate composition. The water may be tap water, but is preferably distilled and/or deionized water. If the water is tap water, it is preferably appropriately filtered in order to remove any undesirable impurities such as organics or inorganics, especially minerals salts which are present in hard water which may thus interfere with the operation of the other constituents of the invention, as well as any other optional components of the liquid concentrates according to the invention.

Water is added in amounts which are sufficient to form the concentrated compositions which amount is sufficient to ensure the retention of a substantially clear characteristic when produced as a concentrate, but at the same time ensuring good blooming upon the addition of the concentrated composition to a further amount of water, or upon the addition of further water to the concentrate.

Other conventional additives known to the art but not expressly enumerated here may also be included in the compositions according to the invention. By way of non-limiting example without limitation these may include: chelating agents, coloring agents, light stabilizers, fragrances, thickening agents, hydrotropes, pH adjusting agents, pH buffers as well as one or more detersive surfactant constituents particularly non-ionic and amphoteric surfactants. Many of these materials are known to the art, per se, and are described in *McCutcheon's Detergents and Emulsifiers*, North American Edition, 1982; *Kirk-Othmer, Encyclopedia of Chemical Technology*, 3rd Ed., Vol. 22, pp. 346–387, the contents of which are herein incorporated by reference. Mixtures of two or more such surface active agents may be incorporated into the inventive compositions. Such optional, i.e., non-essential constituents should be selected so to have little or no detrimental effect upon the desirable characteristics of the present invention, namely the blooming behavior, cleaning efficacy, disinfectant activity, and low toxicity as provided by the inventive compositions. Generally the total weight of such further conventional additives may comprise up to 20% by weight of a concentrated composition formulation.

Further optional, but advantageously included constituents are one or more coloring agents which find use in modifying the appearance of the concentrate compositions and enhance their appearance from the perspective of a consumer or other end user. Known coloring agents, may be incorporated in the compositions in effective amounts. Known art light stabilizer constituents may also be added, particularly wherein coloring agents are used in a composition. As is known to the art, such light stabilizers act to retain the appearance characteristics of the concentrate compositions over longer intervals of time.

Exemplary useful buffers include the alkali metal phosphates, polyphospates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use buffers such materials as aluminosilicates (zeolites), borates, aluminates and certain organic materials such as gluconates, succinates, maleates, and their alkali metal salts. Such buffers keep the pH ranges of the compositions of the present invention within acceptable limits. Desirably however, the compositions of the invention are substantially phosphate free.

Exemplary useful pH adjusting agents include known materials which may be used to adjust the pH of the concentrate compositions to a desired range.

The useful optional nonionic surfactants, include known art nonionic surfactant compounds. Practically any hydrophobic compound having a carboxy, hydroxy, amido, or amino group with a free hydrogen attached to the nitrogen can be condensed with ethylene oxide or with the polyhydration product thereof, such as polyethylene glycol, to form a water soluble nonionic surfactant compound. Further, the length of the polyethylenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides.

Further exemplary useful nonionic surfactants which may be used include certain alkanolamides including monoethanolamides and diethanolamides, particularly fatty monoalkanolamides and fatty dialkanolamides. Commercially available monoethanol amides and diethanol amides include those marketed under the trade names ALKAMIDE and CYCLOMIDE by Rhône-Poulenc Co., (Cranbury, N.J.).

Exemplary useful nonionic surfactants in the compositions according to the present invention include commercially well known surfactant compositions.

Exemplary nonionic surfactants are certain ethoxylates presently commercially available under the trade name NEODOL (Shell Chemical Co., Houston, Tex. (USA)), which are ethoxylated higher aliphatic, primary alcohols Such ethoxylates have an HLB (hydrophobic to lipophilic balance) value of about 8 to 15 and give good oil/water emulsification, whereas ethoxylates with HLB values below 8 contain less than 5 ethylene oxide groups and tend to be poor emulsifiers and poor detergents. Additional satisfactory nonionic surfactant compositions include the condensation products of a secondary aliphatic alcohols containing 8 to 18 carbon atoms in a straight or branched chain configuration condensed with 5 to 30 moles of ethylene oxide. Examples of commercially available nonionic detergents of the foregoing type are those presently commercially available under the trade name of TERGITOL (Union Carbide Co., Danbury, Conn. (USA)).

Other suitable nonionic surfactant compositions include the polyethylene oxide condensates of one mole of alkyl phenol containing from about 8 to 18 carbon atoms in a straight- or branched chain alkyl group with about 5 to 30 moles of ethylene oxide, including those which are presently commercially available under the trade name of IGEPAL (Rhône-Poulenc, Princeton N.J. (USA)). Further useful nonionic surfactants include the water-soluble condensation products of a $C_8$–$C_{20}$ alkanol with a mixture of ethylene oxide and propylene oxide wherein the weight ratio or ethylene oxide to propylene oxide is from 2.5:1 to 4:1, preferably 2.89:1 to 3.3:1, with the total of the ethylene oxide; and propylene oxide (including the terminal ethanol or proponol group) being from 60–85%, preferably 70 to 80%, by weight. Such include those commercially available under the trade name of PLURAFAC (BASF Corp., Hackettstown, N.J. (USA)). Still further useful water-soluble nonionic surfactants include condensation products of a $C_8$–$C_{20}$ alkanols with a mixture of ethylene oxide and/or propylene oxide. Such are commerically available under the tradename POLYTERGENT (Olin Chemical Co., Stamford Conn. (USA)).

Further suitable water-soluble nonionic surfactants which may also be used include those which are marketed under the trade name PLURONICS (BASF Corp., Mt. Olive Township, N.J. (USA)). These are formed by condensing ethylene oxide with a hydrophobic base formed by the condensation of propylene oxide with propylene glycol. Further useful nonionic surfactants include alkylmonoglycosides and alkylpolyglycosides which are alkaline and electrolyte stable. Such are prepared generally by reacting a monosaccharide, or a compound hydrolyzable to a monosaccharide with an alcohol such as a fatty alcohol in an acid medium. Various glycoside and polyglycoside compounds including alkoxylated glycosides may be used. An exemplary useful polyglycoside is one according to the formula:

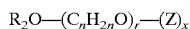

where Z is derived from glucose, R is a hydrophobic group selected from alkyl groups, alkylphenyl groups, hydroxy-alkylphenyl groups as well as mixtures thereof, wherein the alkyl groups may be straight chained or branched, which contain from about 8 to about 18 carbon atoms, n is 2 or 3, r is an integer from 0 to 10, but is preferably 0, and x is a value from about 1 to 8, preferably from about 1.5 to 5. Preferably the alkylpolyglycosides are nonionic fatty alkylpolyglucosides which contain a straight chain or branched chain $C_8$–$C_{15}$ alkyl group, and have an average of from about 1 to about 5 glucose units per fatty alkylpolyglucoside molecule. More preferably, the nonionic fatty alkylpolyglucosides which contain straight chain or branched $C_8$–$C_{15}$ alkyl group, and have an average of from about 1 to about 2 glucose units per fatty alkylpolyglucoside molecule.

A further exemplary group of alkyl glycoside surfactants suitable for use in the practice of this invention may be represented by formula I below:

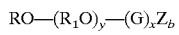

wherein: R is a monovalent organic radical containing from about 6 to about 30, preferably from about 8 to about 18 carbon atoms; $R_1$ is a divalent hydrocarbon radical containing from about 2 to about 4 carbon atoms; O is an oxygen atom; y is a number which has an average value from about 0 to about 1 and is preferably 0; G is a moiety derived from a reducing saccharide containing 5 or 6 carbon atoms; and x is a number having an average value from about 1 to 5 (preferably from 1.1 to 2);

Z is $O_2M^1$,

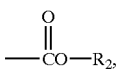

$O(CH_2)$, $CO_2M^1$, $OSO_3M^1$, or $O(CH_2)SO_3M^1$; $R_2$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom, —$CH_2OH$, is oxidized to form a

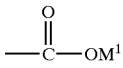

group); b is a number of from 0 to 3x+1 preferably an average of from 0.5 to 2 per glycosal group; p is 1 to 10, $M^1$ is $H^+$ or an organic or inorganic counterion, particularly cations such as, for example, an alkali metal cation, ammonium cation, monoethanolamine cation, or calcium cation.

As defined in Formula I above, R is generally the residue of a fatty alcohol having from about 8 to 30 and preferably 8 to 18 carbon atoms. Examples of such alkylglycosides as described above include, for example, APG™ 325 CS GLYCOSIDE which is described as being a 50% $C_9$–$C_{11}$ alkyl polyglycoside, also commonly referred to as D-glucopyranoside, (commercially available from Henkel Corp, Ambler Pa.) and Glucopon™ 625 CS which is described as being a 50% $C_{10}$–$C_{16}$ alkyl polyglycoside, also commonly referred to as a D-glucopyranoside, (available from Henkel Corp., Ambler Pa.).

The nonionic surfactants, when present, can be present either singly, or as a mixture of two or more nonionic surfactant compounds as defined above.

As further useful optional constituent, the inventive compositions may also include one or more further known art surfactant compositions, including betaines, ethylene oxide condensates, fatty acid amides, and amine oxide semi-polar nonionic surfactants.

Exemplary useful betaine surfactants include those according to the general formula:

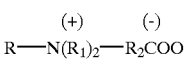

wherein R is a hydrophobic group selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring being treated as equivalent to about 2 carbon atoms, and similar structures interrupted by amido or ether linkages; each $R_1$ is an alkyl group containing from 1 to about 3 carbon atoms; and $R_2$ is an alkylene group containing from 1 to about 6 carbon atoms.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate.

Useful fatty acid amides include those which are known to the art. Particular exemplary fatty acid amide surfactants include ammonia, monoethanol, and diethanol amides of fatty acids having an acyl moiety which contains from about 8 to about 18 carbon atoms, and which may be represented in accordance with the formula:

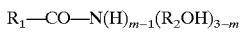

where $R_1$ represents a saturated or unsaturated aliphatic hydrocarbon radical of from about 7 to 21 carbon atoms, but preferably from about 11 to 17 carbon atoms; $R_2$ represents a —$CH_2$— or —$CH_2CH_2$—, and m is an integer from 1 to 3, but is preferably 1. Preferably, $R_1$ is a saturated or unsaturated aliphatic hydrocarbon radical comprising from about 11 to 17 carbon atoms, and m is 1.

Further examples of such compounds include monoethanol amine coconut fatty acid amide and diethanol amine dodecyl fatty acid amide. An exemplary useful fatty acid amide includes cocomonoethanol amide or cocodiethanolamide, which are presently commercially available as MONAMID CMA or MONAMID MDNA (both from Mona Industries, Paterson N.J. (USA)).

Known art amine oxide semi-polar nonionic may be included in the present inventive compositions. Non-limiting examples of useful amine oxide semi-polar nonionic surfactants include those according to the formula:

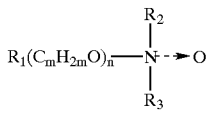

wherein $R_1$ is an alkyl, 2-hydroxyalkyl, 3-hydroxyalkyl, or 3-alkoxy-2-hydroxypropyl radical where the alkyl and alkoxy parts contain from about 8 to about 18 carbon atoms, $R_2$ and $R_3$ are independently selected from methyl, ethyl, propyl, isopropyl, 2-hydroxyethyl, 2-hydroxypropyl, or 3-hydroxypropyl, m is an integer from 2 to 4, and n is an integer from 0 to about 10. Preferably, the amine oxide semi-polar nonionic surfactants are those according to the formula immediately preceeding wherein $R_1$ is an alkyl radical of from 12 to 16 carbon atoms, $R_2$ and $R_3$ are independently selected from methyl or ethyl, m is 2, and n is 0.

Examples of such useful amine oxide semi-polar nonionic surfactants include cetyl-, myristyl- or lauryl- dimethyl amine oxide or mixtures thereof.

These compositions may be used individually, or may be used in mixtures. According to preferred embodiments of the invention, an amine oxide is present.

What is to be understood by the term "concentrate" and "concentrate composition" in this specification and claims is the pre-consumer dilution and composition of the cleaning composition which is the essentially the form of the product prepared for sale to the consumer or other end user. Such a consumer or other end user would then normally be expected to dilute the same with water to form a cleaning composition. It is to be understood however that nothing in this invention would bar its use as cleaning composition without any further dilution and it may be used in the concentrations in which it was prepared for sale. Similarly, what is to be understood by the term "cleaning compositions" are the water diluted compositions which are expected to be prepared by the consumer or other end user by mixing a measured amount of the "concentrate" with water in order to form an appropriately diluted cleaning composition which is suitable for use in cleaning applications, especially in the cleaning of hard surfaces.

It is also to be understood, that proportions of one or more constituents have been and generally are referred to as percent by weight or as parts by weight based on a measure of 100% by weight, unless otherwise indicated.

It is particularly surprising that the concentrate compositions according to the present invention exhibit a blooming characteristic when added to a larger volume of water, particularly in the ratios of concentrate composition:water described herein. As discussed previously, blooming is generally associated with pine oil containing compositions. In the compositions of the present invention, pine oil is most desirably absent.

According to certain particularly preferred embodiments of the invention there is provided an aqueous concentrated liquid disinfectant composition which blooms when added to a larger volume of water which comprises, most desirably consists essentially of, the following constituents:

a germicidally effective amount of an antiseptic constituent other than a germicidal cationic surfactant, especially where the antiseptic is TRICLOSAN;

0.1–35% wt. of an organic solvent constituent, preferably both an alkylene glycol and a monohydric lower aliphatic alcohol 0.1–12% wt. of a binary co-solvent system comprising an alkyl biphenyl solvent and a co-solvent;

1–20% wt. of an amine oxide;

to 100% wt. water, and;

optionally but desirably, 1–5% of a carboxylate constituent;

further optionally but desirably up to 20% wt. of at least one optional constituent selected from: chelating agents, coloring agents, light stabilizers, fragrances, thickening agents, hydrotropes, pH adjusting agents, pH buffers as well as one or more detersive surfactant constituents particularly non-ionic and amphoteric surfactants, as well as others known the art.

As generally denoted above, the formulations according to the invention include both cleaning compositions and concentrates as outlined above which differ only in the relative proportion of water to that of the other constituents forming such formulations. While the concentrated form of the cleaning compositions find use in their original form, they are more frequently used in the formation of a cleaning composition therefrom. Such may be easily prepared by diluting measured amounts of the concentrate compositions in water by the consumer or other end user in certain weight ratios of concentrate:water, and optionally, agitating the same to ensure even distribution of the concentrate in the water. As noted, the concentrate may be used without dilution, i.e., in concentrate:water concentrations of 1:0, to extremely dilute dilutions such as 1:10,000. Desirably, the concentrate is diluted in the range of 1:0.1 –1:1000, preferably in the range of 1:1–1:500 but most preferably in the range of 1:10–1:100. The actual dilution selected is in part determinable by the degree and amount of dirt and grime to be removed from a surface(s), the amount of mechanical force imparted to remove the same, as well as the observed efficacy of a particular dilution. Generally better results and faster removal is to be expected at lower relative dilutions of the concentrate in water.

In accordance with preferred embodiments of the invention, when a quantity of the concentrate compositions taught herein are added to a larger volume of water, a blooming characteristic is manifested. Such "blooming" may be broadly characterized as the formation of milky, creamy or cloudy appearance which is manifested when a dilutable composition is added to a larger volume or quantity of water. Such "blooming" may be alternately characterized as the reduction of transmitted light through an amount of water by at least 30%, desirably by at least 40%, yet more desirably by at least about 50%, and yet most desirably by at least 60% or more when a dilution of the concentrate composition:water with the weight or volume ratio range of from 1:64–102 is formed. That such blooming may be attained without the use of pine oil fractions as is common in certain commercially available pine oil containing preparations is surprising.

As has been noted, concentrate compositions according to preferred embodiments of the invention exhibit a long lasting blooming effect when they are diluted into a larger volume of water, especially when used to form (weight ratio) dilutions with water of concentrate:water of 1:64 at room temperature. Desirably, such dilutions do not exhibit an increase in light transmittance in accordance with the measurement methods discussed in the Examples below, of more than 50% (based on the initial 'as mixed' value) during its initial three-day interval.

The concentrate compositions according to the invention, and aqueous dilutions formed therefrom, are particularly useful in the sanitization of hard surfaces. By way of non-limiting example, hard surfaces include surfaces composed of refractory materials such as: glazed and unglazed tile, brick, porcelain, ceramics as well as stone including marble, granite, and other stones surfaces; glass; metals; plastics e.g. polyester, vinyl; fiberglass, FORMICA, CORIAN and other hard surfaces known to the art. Hard surfaces which are to be particularly denoted include those associated with kitchen environments, lavatory environments, especially flooring surfaces and the surfaces of fixtures (doors, cabinets, shelving, and the like) in such environments.

The compositions according to the invention exhibit sanitizing properties, and are useful in the sanitization of surfaces wherein the presence of various viruses, molds, fungi, bacteria, and mildew are suspected.

In preferred embodiments, aqueous dilutions of the concentrated aqueous liquid disinfectant compositions exhibit antimicrobial efficacy against at least one of the following bacteria: *Staphylococcus aureus, Escherichia coli., Pseudomonas aeruginosa*, where the ratio of concentrate composition:water is 1:64 to 1:102. According to more preferred embodiments, aqueous dilutions of the concentrated aqueous liquid disinfectant compositions exhibit antimicrobial efficacy against at least two of the following bacteria: *Staphylococcus aureus, Escherichia coli., Pseudomonas aeruginosa*, where the ratio of concentrate composition:water of 1:64 to 1:102. Such aqueous dilutions may be classified as "broad spectrum disinfectant" compositions. According to a still more preferred embodiment, aqueous dilutions of the concentrated aqueous liquid disinfectant compositions exhibit antimicrobial efficacy against all three of the following bacteria: *Staphylococcus aureus, Escherichia coli, Pseudomnonas aeruginosa*, where the ratio of concentrate composition:water of 1:64 to 1:102. Such aqueous dilutions may be classified as "hospital strength disinfectant" compositions. In each of these respective preferred, more preferred and still more preferred embodiments described immediately above, those which exhibit antimicrobial efficacy at greater aqueous dilutions of the concentrated aqueous liquid disinfectant compositions in water, such as at concentrate:water dilution ratios ratios of 1:102, are preferred over concentrate:water dilution ratios of 1:85, and still more preferred over concentrate:water dilution ratios of 1:64.

Such dilution ratios of concentrate:water as described above may be volume/volume basis, or a weight/weight basis.

The following examples below illustrate exemplary and among them preferred formulations of the composition according to the instant invention. It is to be understood that these examples are presented by means of illustration only and that further useful formulations fall within the scope of this invention and the claims may be readily produced by one skilled in the art and not deviate from the scope and spirit of the invention.

EXAMPLES

A number of formulations were produced by mixing the constituents outlined in Table 1 by adding the individual constituents into a beaker of deionized water at room temperature which was stirred with a conventional magnetic stirring rod. The order of addition is not critical, but good results are obtained where the surfactants are added to the water prior to the remaining constituents. Stirring continued until the formulation was homogenous in appearance. It is to be noted that the constituents might be added in any order, but it is preferred that water be the initial constituent provided to a mixing vessel or apparatus as it is the major constituent and addition of the further constituents thereto is convenient. The exact compositions of the example formulations are listed on Table 1, below.

TABLE 1

|  | Ex.1 | Ex.2 | Ex.3 | Ex.4 |
|---|---|---|---|---|
| isopropyl alcohol | 12.0 | 12.0 | 12.0 | 12.0 |
| lauryl alcohol | 1.0 | 1.0 | 1.0 | 1.0 |
| propylene glycol | 20.0 | 20.0 | 20.0 | 20.0 |
| biphenyl solvent A | 2.8 | 2.1 | 2.45 | 2.0 |
| amine oxide | 14.0 | 14.0 | 14.0 | 14.0 |
| carboxylate | — | — | — | 1.0 |
| antiseptic | $1.2^{(1)}$ | $0.9^{(1)}$ | $1.05^{(1)}$ | $1.33^{(2)}$ |
| Na2EDTA | 0.5 | 0.5 | 0.5 | — |
| EDTA | — | — | — | 0.5 |
| Colorant | 3.0 | — | — | — |
| di water | q.s. | q.s. | q.s. | q.s. |

All of the formulations on Table 1 indicated in weight percent, and the percent actives of individual constituents are 100% unless otherwise indicated. Water was added in 'quantum sufficient' to provide 100% wt. of the concentrate compositions according to Table 1. The identity of the constituents indicated on Table 1 are described more fully on Table 2, following:

TABLE 2

| | |
|---|---|
| isopropyl alcohol | propan-2-ol (Eastman Chem. Co.) |
| lauryl alcohol | technical grade mixture of 65–75% wt. 1-dodecanol, 22–28% wt. 1-tetradecanol, 4–8% wt. 1-hexadecanol, and 0–0.5% wt. 1-decanol (Henkel_Corp.) |
| propylene glycol | 1,2-propane-diol |
| biphenyl solvent A | NUSOLV ABP-103 (Arristec, Inc.) is a mixture of alkyl biphenyls |
| biphenyl solvent B | SURE SOL 300 (Koch Chemical Co.) is a mixture of alkyl biphenyls, specifically diisopropyl biphenyls (65%), triisopropyl biphenyls (30%) and other alkyl biphenyls (5%) |
| biphenyl solvent C | SURE SOL 300 (Koch Chem. Co.) is a mixture of alkyl biphenyls |
| amine oxide | bis-(2-hydroxyethyl C12–C15 alkyloxypropyl) amine oxide, as AO-728 Special (50% wt. of) from Tomah Inc. |
| carboxylate | carboxlated alcohol, as EMCOL CNP 110 (Witco Chem. Co.), 100% wt. Actives |
| antiseptic[(1)] | 2,4,4'-trichloro-2'-hydroxydiphenyl ether (100% wt. actives) as TRICLOSAN (Ciba-Geigy Inc.) |

TABLE 2-continued

| | |
|---|---|
| antiseptic[2] | orthobenzylparachlorophenol, in isopropanol as a carrier (75% wt. actives), from Bayer Chem. Co. |
| Na2EDTA | disodium salt of ethylenediamine tetraacetic acid, sold as VERSENE Na2 crystal (Dow Chem. Co.) |
| EDTA | tetrasodium salt of ethylendiaminetetraacetic acid |
| Colorant | aqueous caramel solution, 1% wt. caramel, as a coloring agent |
| di water | deionized water |

The blooming characteristics of these formulations was characterized by using the Brinkman Sybron PC 801 calorimeter. Each tested formulation were diluted with deionised water in a weight ratio of 1:64, and the test was carried out with each of the formulations and water at room temperature (68° F., 20° C.). The resulting determined values, reported as "blooming" in the following table provide an empirical evaluation in percent transmittance (%) of the degree of transparency of a diluted example formulation wherein 0% indicates complete opacity and 100% the transparency of a deionised water sample. The result was tabulated on Table 3 as follows:

TABLE 3

| Formulation: | % Transmittance |
|---|---|
| Comp.1 | 0.5 |
| Ex.1 | 0.8 |
| Ex.2 | 1.7 |
| Ex.3 | 1.0 |
| Ex.4 | 2.3 |

Comparative 1 (Comp.1) was DETTOL (Reckitt & Colman PLC, Hull, UK), a soap based, blooming type disinfecting concentrate composition which does not include biphenyl solvents. DETTOL has a particularly substantive bloom and is used as a 'benchmark' for other formulations.

The formulation according to comparative example 2 (Comp.2) was a control formulation which did not contain a biphenyl solvent, but which have an blooming characteristic. Formulations according to the invention which included the biphenyl solvent excellent blooming characteristics.

Antimicrobial Efficacy

A modified European suspension test was carried out for the formulation according to Example 1 described above, and as a comparative example, DETTOL (Reckitt & Colman PLC, England). The method is summarized as follow.

1) Pipette 8 ml of the test product dilution into sterile medicant tube and held at 20C+1C in water bath.
2) In another sterile medicant tube pipette 1.0 ml of adjusted culture and 1.0 ml of prepared Bovine Albumin Solution and held at 20C+1C in water bath.
3) At time=0 minute, add product solution into medicant tube containing a mixture of Bovine Albumin Solution and culture suspension of each test organism. This mixture results in a final dilution of the test product, a concentration of 0.03% of Bovine Albumin Solution and bacterial count of at least 1–3×10^7 CFU/ml.
4) At time=5 minutes, pipette 1 ml of this mixture into 9 ml of neutralizing solution (letheen broth) so as to achieve 1:10 dilution. Prepare serial dilution in Letheen broth and place with Tryticase soy with lecithin and Tween 80 agar in duplicate. Control: The procedure as outlined above was repeated, using 8 ml of sterile water instead of product dilution for each test organism.

To pass the test method, it was required that the tested formulations satisfy a 3 log reduction in reference bacterial strain of Ps.aeruginosa (ATTC #15442) with 5 minutes contact time at 20° C.+1° C. according to the defined testing method.

It was found that each of the formulations according to Examples 1 and 4 showed complete reduction of the test organisms at the testing contact time. The testing requirements indicate a (great than) ">3" log reduction within 5 minutes. It was concluded that example formulations had similar microbial activity as DETTOL.

Cleaning Test:

Cleaning efficacy was measured for weight ratios of 1:64 (concentrate composition:water) aqeuous dilutions of formulations according to Examples 3 and 4, and as a control, the formulation according to Comp.1 described above. The test was carried out using the ASTM D4488–89, Annex A2 method—greasy soil on painted masonite wallboard test, using a Gardner Washability Apparatus.

Latex painted masonite wallboard is soiled with a mixture of melted, oily soils containing a small amount of carbon black and allowed to set overnight. A first aqueous dilution is applied to a sponge that scrubs half the soiled substrate in a straight-line using the Gardner Washability Apparatus. Afterwards, the second aqueous dilution is applied to a further sponge that scrubs the other half of the soiled substrate in a similar manner.

In determining the cleaning efficiency, reflectance values were determined using a Gardner Lab Scan Reflectometer for each of the following: a clean unsoiled panel, a soiled panel, and a soiled panel following Gardner Washability Apparatus scrubbing. Such reflectance values were then employed to calculate % cleaning efficiency according to the following formula:

$$\% \text{ Cleaning Efficiency} = \frac{Lt - Ls}{Lo - Ls} \times 100\%$$

wherein,

Lt=% reflectance average after scrubbing solid tile

Ls=% reflectance average before cleaning soiled tile

Lo=% reflectance average original tile before soiling

Cleaning efficiency results for Formulation 1 are shown in Table 4, hereinafter.

TABLE 4

| Test # | Formulation: water (1:64) w/w dilution | unsoiled reflectance (Lo) | soiled reflectance (Ls) | After scrubbing reflectance (Lt) | % Cleaning Efficiency |
|---|---|---|---|---|---|
| 1 | Comp. 1 | 93.46 | 27.10 | 59.52 | 48.9 |
| 2 | Ex. 3 | 93.46 | 27.10 | 60.60 | 50.5 |
| 3 | Ex. 4 | 93.46 | 27.10 | 59.72 | 49.2 |

As shown, the measurement of the cleaning effectiveness of the test samples involved the ability of the cleaning composition to remove the test soil from the test substrate. This was expressed by % Cleaning Efficiency. As numerical values for a % Cleaning Efficiency increase, higher cleaning effectiveness is achieved for the cleaning composition tested. As the results show, the inventive compositions showed an excellent cleaning property.

We claim:

1. An aqueous concentrated liquid disinfectant composition which blooms when added to a larger volume of water, said composition comprising:

a germicidally effective amount of an antiseptic constituent other than a quaternary ammonium compound;

an organic solvent constituent;

a binary co-solvent system comprising alkyl biphenyl solvent and a co-solvent;

optionally, at least one constituent selected from the group consisting of chelating agents, coloring agents, light stabilizers, fragrances, thickening agents, hydrotropes, pH adjusting agents, pH buffers, and one or more detersive surfactant constituents particularly non-ionic and amphoteric surfactants; and the balance, water.

2. The composition according to claim 1 wherein the antiseptic is selected from the group consisting of chloramine, iodine, iodophors, water soluble salts of chlorhexidine, parachloro meta xylenol, hexachlorophene, 2-bromo-2-nitropropane diol, salicylanilide, 3',4',5-trichlorosalicylanilide, 3,5-dibromo-3'-trifluoromethyl salicylanilide, 3,4,4'-trichlorocarbamilide, and 2,4,4'-trichloro-2'-hydroxydiphenyl ether.

3. The composition according to claim 2 wherein the antiseptic is 2,4,4'-trichloro-2'hydroxydiphenyl ether.

4. The composition according to claim 1 wherein the alkyl biphenyl solvent is represented by the structure:

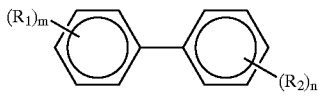

wherein:

$R_1$ is hydrogen or is a lower alkyl radical, preferably a $C_1$–$C_{10}$ straight chained or branched alkyl radical, $R_2$ is a lower alkyl radical, preferably a $C_1$–$C_{10}$, straight chained or branched alkyl radical, m is an integer from 1 to 3 inclusive, and n is an integer from 1 to 3 inclusive.

5. The composition according to claim 4 wherein:

$R_1$ is hydrogen or a $C_1$–$C_6$ straight chained or branched alkyl radical, and $R_2$ is a $C_1$–$C_6$ straight chained or branched alkyl radical.

6. The composition according to claim 5 wherein:

$R_1$ is hydrogen, and m is 1.

7. The composition according to claim 1 in which the organic solvent constituent comprises an alkylene glycol and a monohydric lower aliphatic alcohol.

8. An aqueous concentrated liquid disinfectant composition which blooms when added to a larger volume of water, said composition comprising:

a germicidally effective amount of an antiseptic other than a quaternary ammonium compound;

0.1–35% wt. of an organic solvent constituent comprising an alkylene glycol and a monohydric lower aliphatic alcohol;

0.2–4% wt. of a binary co-solvent system comprising an alkyl biphenyl solvent and a co-solvent;

optionally, up to 20% wt. of a least one constituent selected from the group consisting of chelating agents, coloring agents, light stabilizers, fragrances, thickening agents, hydrotropes, pH adjusting agents, pH buffers, and one or more detersive surfactant constituents particularly non-ionic and amphoteric surfactants; and the balance, water.

9. A concentrated composition according to claim 8 characterized in that, when said composition is diluted with water at a weight ratios of concentrate:water of 1:64 at room temperature, the resultant composition exhibits a reduction in light transmittance of at least 50%.

10. A method for disinfecting a hard surface where the presence of Gram positive or Gram negative bacteria is suspected, which method comprises the step of contacting the hard surface with a disinfecting effective amount of a composition according to claim 9.

* * * * *